United States Patent
Gordziel (12)

(10) Patent No.: US 6,306,904 B1
(45) Date of Patent: Oct. 23, 2001

(54) ANTIHISTAMINIC/ANTITUSSIVE COMPOSITIONS

(75) Inventor: Steven A. Gordziel, Belle Mead, NJ (US)

(73) Assignee: Carter-Wallace, Inc., New York, NY (US)

( * ) Notice: Subject to any disclaimer, the term of this patent is extended or adjusted under 35 U.S.C. 154(b) by 0 days.

(21) Appl. No.: 09/625,422

(22) Filed: Jul. 25, 2000

(51) Int. Cl.⁷ .................. A61K 31/216; A61K 31/4402
(52) U.S. Cl. ............................................. 514/530; 514/352
(58) Field of Search ...................................... 514/530, 352

(56) References Cited

FOREIGN PATENT DOCUMENTS

06287144 * 10/1994 (JP) .

* cited by examiner

Primary Examiner—Phyllis G. Spivack
(74) Attorney, Agent, or Firm—Kevin B. Clarke

(57) ABSTRACT

Tannate compositions consisting essentially of carbetapentane tannate and pyrilamine tannate which are effective when administered orally for the symptomatic relief of coryza associated with the common cold, sinusitis, allergic rhinitis, unproductive cough and upper respiratory tract conditions are disclosed.

6 Claims, No Drawings

ANTIHISTAMINIC/ANTITUSSIVE COMPOSITIONS

FIELD OF INVENTION

The invention relates to novel antihistaminic and antitussive tannate compositions. The compositions contain as essential ingredients carbetapentane tannate and pyrilamine tannate.

BACKGROUND OF INVENTION

A considerable number of tannic acids occur in nature. Chemically, these acids are described as polymers of different hydroxybenzoic acids. Generally, when the term tannic acid is employed, as in the present case, the acid referred to is gallotannic acid, the internal ester of gallic acid also frequently referred to as tannin.

Tannic Acid consists of an amorphous powder glistening scales or spongy masses varying in color from yellowish-white to light brown. Tannic acid is very soluble in water, glycerine or alcohol.

Tannic acids are usually obtained from glycosides which consist of several molecules of a tannic acid in combination with glucose.

Commercially available, tannic acid, also known as Tannin, has a complex non-uniform chemistry usually contains from about 5% to about 10% by weight water, has a molecular weight of about 1700 and is typically produced from Turkish or Chinese nutgall.

Carbetapentane, 2-(2-diethylaminoethoxy)ethyl-1 phenylcyclopentane carboxlate is an antitussive compound that is described in U.S. Pat. No. 2,842,585 and is structurally related to caramiphen. Carbetapentane citrate has a melting point of 93° C. and occurs as a white powder freely soluble in water and slightly soluble in alcohol.

Carbetapentane has an atropine-like action that depresses the cough reflex by selective central nervous system depression.

Pyrilamine is one of the oldest and most enduring antihistaminic drugs, known chemically as N-[(4-methoxyphenyl)methyl]-N',N'-dimethyl-N-2-pyridinyl-1,2-ethanediamine, its preparation is disclosed in U.S. Pat. No. 2,502,151 and is an oily liquid. Pyrilamine hydrochloride salt is very soluble in water and has a melting point of 143–143.50° C. whereas the maleate salt is slightly soluble in water, benzene and ether and has a melting point of 100–101° C.

Antihistamine compounds in the form of their free bases as well as their salts, e.g. hydrochloride, citrate, maleate, tannate, etc., are well known. Antihistamines in the form of their tannate salts are very desirable because such salts are generally stable and may be combined in such form without any untoward side effects.

Antihistaminics and antitussives in the form of their tannate salts are typically prepared by reacting the free base, e.g. pyrilamine, carbetapentane, etc. with tannic acid in the presence of a volatile solvent, usually isopropanol. Typically, in the conventional isopropanol route, the decongestant or antihistaminic free base and the tannic acid will be present in the isopropanol at a concentration of about 20% based on the weight of the reaction mixture. The reaction mixture is stirred for about one hour while maintaining the mixture at 60–70° C. The reaction mixture is cooled to room temperature and then filtered, washed with isopropanol and then vacuum dried. Alternative routes to the tannate salts are described in U.S. Pat. Nos. 5,599,846 and 5,663,415.

THE INVENTION

It has now been found that the novel combination of carbetapentane tannate and pyrilamine tannate produces a composition having antitussive and antihistaminic properties superior to the use of either one of the tannate compounds alone.

The compositions of the present invention may be prepared for oral administration in the form of powders, capsules, elixirs, syrups and the preferred forms of tablets formulated so that ideally each tablet contains about 50 mg to about 75 mg, preferably about 60 mg of carbetapentane tannate and about 50 mg to about 75 mg, preferably about 60 mg pyrilamine tannate or suspensions formulated so that ideally each 5 mL (approximately 1 teaspoon) of suspension would contain approximately 20 to 30 mg carbetapentane tannate and an equal amount of pyrilamine tannate.

Tablets containing the unique tannate combination of the present invention are prepared in a conventional manner by the addition of suitable pharmaceutical carriers including fillers, diluents, colorants, lubricants and the like as well as conventional and well known binding and disintegrating agents. A typical tablet composition of the present invention containing starch, dibasic calcium phosphate, coloring, magnesium stearate, methylcellulose, polygalacturonic acid, povidone and talc as described in Example 1 which follows is prepared by well known conventional tabletting techniques such as those disclosed in U.S. Pat. Nos. 3,018,221; 2,798,024 and 2,757,124.

EXAMPLE 1

Carbetapentane Tannate and Pyrilamine Tannate Tablets

| Ingredient | Milligrams per Tablet |
| --- | --- |
| Carbetapentane Tannate | 60.0 |
| Pyrilamine Tannate | 60.0 |
| Starch, NF | 65.0 |
| Methylcellulose, USP | 150 |
| polygalacturonic Acid | 32.0 |
| Dibasic Calcium Phosphate, USP, Dihydrate | 65.0 |
| Povidone, USP | 25.0 |
| Talc, USP | 5.4 |
| FD&C Red #40 Aluminum Lake-40% | 3.93 |
| D&C Blue #1 Aluminum Lake-29% | 1.0 |
| Magnesium Stearate, NF | 4.0 |
| Alcohol Specially Denatured 23A 190 Proof | 140[1] |

[1]Not present in the finished tablet product

Suspensions of the compositions of the present invention are prepared in a conventional manner such that each 5 mL (one teaspoon) contains:

| | |
| --- | --- |
| Carbetapentane Tannate | 20–30 mg |
| Pyrilamine Tannate | 20–30 mg |

The suspension formulations additionally contain benzoic acid, coloring, natural and artificial flavors, glycerin, kaolin, magnesium aluminum silicate, methyl paraben, pectin, purified water, saccharin, sodium hydroxide, tannic acid and sucrose or sorbitol.

Example 2, which follows, is illustrative of a typical suspension formulation of the present invention prepared by conventional well known compounding techniques.

EXAMPLE 2

| Ingredient | Milligrams per 5 mL |
| --- | --- |
| CarbetapentaneTannate | 30.0 |
| Pyntamine Tannate | 30.0[1] |
| Pectin, USP (Medium Viscosity) | 50.0 |
| Kaotin, USP (Colloidal Powder) | 1000 |
| Magnesium Aluminum Siticate, NF | 35.0 |
| Benzoic Acid, USP | 10.0 |
| Methytparaben, NF | 5.0 |
| Sucrose, NF | 1000 |
| Saccharin Sodium, USP | 0.75 |
| Glycerin, USP | 225 |
| Flavor Black Currant Imitation | 0.91 |
| Flavor Strawberry with Other Natural Flavors | 2.28 |
| Purple Shade "R" Dye | 0.45 |
| FD&C Red #3 Dye | 0.8 |
| FD&C Yellow #5 | 0.3 |
| Sodium Hydroxide Sotution-50% | 3.17[2] |
| Purified Water, USP (Deionized) adjust to | 5 ml |

[1] 5% excess added during manufacturing
[2] The quantity of Sodium Hydroxide Solution may be varied depending on the pH of the Kaolin used in the batch. Tannic acid may also be used in lieu of sodium hydroxide solution for pH adjustment.
[3] Sodium Citrate, USP, Dihydrate and Citric Acid, usp, Anhydrous may also be included in the formula for pH adjustment.

For the purpose of this disclosure, a warm-blooded animal is a member of the animal kingdom possessed of a homeostatic mechanism and includes mammals and birds.

The dosage administered will be dependent on the age, health and weight of the recipient, kinds of concurrent treatment, if any, frequency of treatment and effect desired.

It should be understood that the above examples are illustrative of the best mode only of the invention herein disclosed. Given the present disclosure, it is anticipated that numerous variations will occur to those skilled in the art. A latitude of modification, substitution and change is intended and in some instances, some features of the invention will be employed without a corresponding use of other features. Accordingly, it is intended that the spirit and scope of the invention disclosed herein should be limited only by the following claims.

What is claimed is:

1. A therapeutic composition for the symptomatic treatment of coryza associated with the common cold, sinusitis, allergic rhinitis, unproductive cough and upper respiratory tract conditions in warm-blooded animals in need of such treatment said composition comprising pharmaceutically effective amounts of active ingredients, wherein said active ingredients consist of carbetapentane tannate and pyrilamine tannate.

2. A therapeutic composition as claimed in claim 1 in tablet form.

3. A therapeutic composition as claimed in claim 1 in suspension form.

4. A method for symptomatically treating and relieving the distress of coryza associated with the common cold, sinusitis, allergic rhinitis, unproductive cough and upper respiratory tract conditions in warm-blooded animals which comprises orally administering to a warm-blooded animal in need of such treatment a therapeutic amount of a composition comprising active ingredients, wherein said active ingredients consist of carbetapentane tannate and pyrilamine tannate.

5. A method as claimed in claim 4 wherein said composition is in tablet form.

6. A method as claimed in claim 4 wherein said composition is a suspension.

* * * * *